(12) United States Patent
Besse

(10) Patent No.: US 6,168,613 B1
(45) Date of Patent: Jan. 2, 2001

(54) THERMAL COMPRESS AND HOLDER

(76) Inventor: Suzanne Besse, 2122 Park Pl., Boca Raton, FL (US) 33486

( * ) Notice: Under 35 U.S.C. 154(b), the term of this patent shall be extended for 0 days.

(21) Appl. No.: 09/275,601

(22) Filed: Mar. 24, 1999

(51) Int. Cl.[7] ............................................ A61F 7/00
(52) U.S. Cl. ................................ 607/114; 607/108
(58) Field of Search ....................... 607/96, 104, 108, 607/111, 114; 5/644

(56) References Cited

U.S. PATENT DOCUMENTS

| | | |
|---|---|---|
| 3,893,834 | 7/1975 | Armstrong . |
| 4,462,224 | 7/1984 | Dunshee et al. . |
| 4,756,311 | 7/1988 | Francis, Jr. . |
| 5,111,810 | 5/1992 | Fortney . |
| 5,230,333 * | 7/1993 | Yates et al. ........................ 607/111 |
| 5,584,086 * | 12/1996 | VanWinkle et al. ................... 5/644 |

* cited by examiner

Primary Examiner—Linda C. M. Dvorak
Assistant Examiner—R. Kearney
(74) Attorney, Agent, or Firm—Oppedahl & Larson LLP

(57) ABSTRACT

This invention relates to a thermal compress and holder which has opposed pockets for receiving the thermal compress and a user's hand. The compress is preferably in a novelty character shape, in which case the holder resembles a sleeping bag with the novelty character's head peering out.

15 Claims, 2 Drawing Sheets

THERMAL COMPRESS AND HOLDER

BACKGROUND OF THE INVENTION

1. Field of the Invention

This invention relates to a thermal compress and holder having separate chambers for holding a thermal compress, preferably in the shape of a novelty character and for inserting the user's hand. The holder allows the user to position the thermal compress over a site of injury while protecting the user's hand and the injury site from direct contact with the hot or cold compress.

2. Description of the Related Art

Thermal compresses including a plastic envelope containing a gel capable of maintaining gel-like properties over a wide temperature range are known in the art. Thermal compresses capable of withstanding heating by microwave are also known as evidenced by U.S. Pat. No. 4,756,311. Thermal compresses which are chilled in a freezer and which provide prolonged cooling are also known, and have been made in a variety of shapes, including novelty animal shapes. Instant hot or cold packs in which a chemical reaction creates the temperature change are also known as evidenced by U.S. Pat. No. 4,462,224. These thermal compresses are characterized in that no outside heat or cold source is required, and are generally single-use items because the chemical reaction is not reversible.

In use, conventional thermal compresses are placed on the site of injury and held by the user or, in the case of child, by a parent or helper. The outer plastic envelope of the compresses are generally not insulated, causing the user's hand to be in direct contact with the hot or cold compress. To reduce the discomfort of holding a hot or cold compress, a towel or other covering may be placed over the thermal compress. The user often places a similar covering between the skin of the injured area and the thermal compress to avoid burning or freezing the skin.

The use of conventional thermal compresses on children is awkward as an adult must generally hold the compress and care must be taken to avoid burning or freezing the child's skin. Further, the amount of pressure applied may be too great or insufficient, since the adult does not sense what the child it feeling.

Accordingly, there is a need for a thermal compress suitable for use on children, that is insulated and easy for a child or parent to use, and is comforting to the child. It is an object of the present invention to provide such a thermal compress in combination with a holder.

SUMMARY OF THE INVENTION

The thermal compress and holder of the invention are designed to be easily held by a child or adult. The thermal compress and holder are designed to avoid burning or freezing the skin on which they are placed as well as to protect the user's hand. Furthermore, in a preferred embodiment, the compress and the holder are designed to have a pleasing and comforting appearance for children. In a further embodiment, the compress and/or holder are designed as characters known to children to provide comfort to a child.

In accordance with the instant invention, a conventional thermal compress is disposed within a holder. The holder has two pockets, one for receiving the compress and a second for receiving the hand of the user. The two pockets are separated by an insulated member, so that the user's hand placed in one pocket is thermally isolated from a thermal compress placed within the other pocket.

In a preferred embodiment of the invention, the thermal compress has a novelty shape, for example the shape of an animal or cartoon character, having a definite head portion. In this case, the holder is sized so that the head portion of the thermal compress extends out of the holder, making the combination of the thermal compress and the holder into a kind of puppet which can be used to provide emotional comfort at the same time that therapeutic heating or cooling is made available.

DETAILED DESCRIPTION OF THE INVENTION

Figure 1:
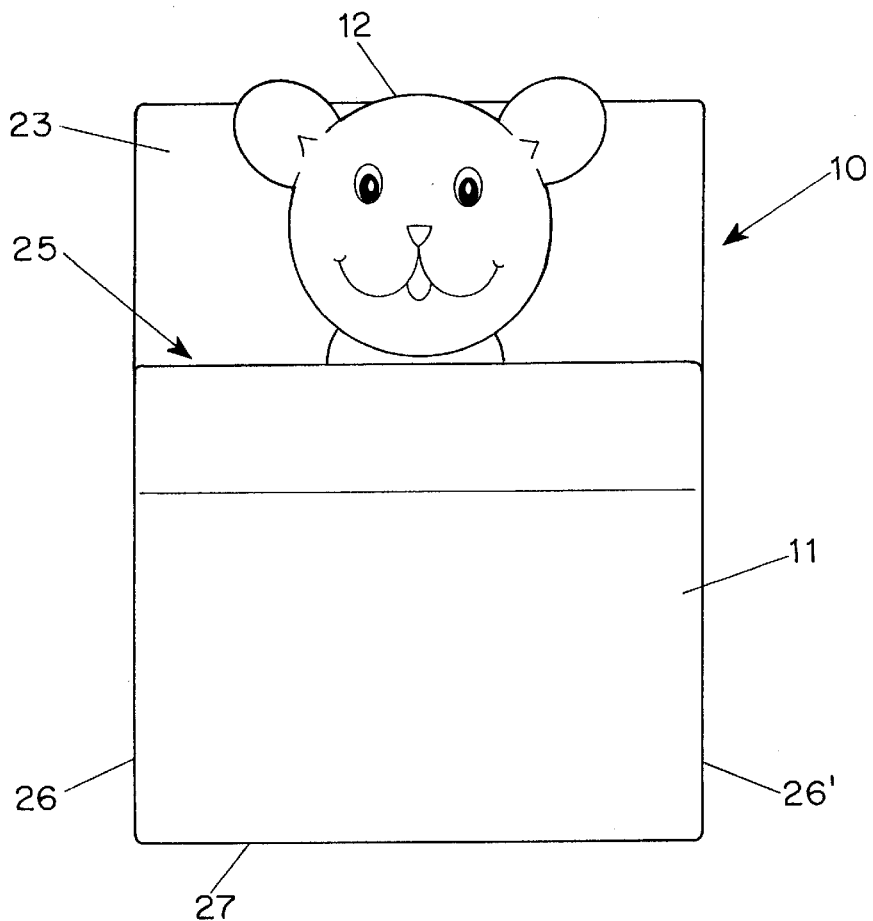
FIG. 1 is a top view of a novelty thermal compress and holder in accordance with the invention.
Figure 2:
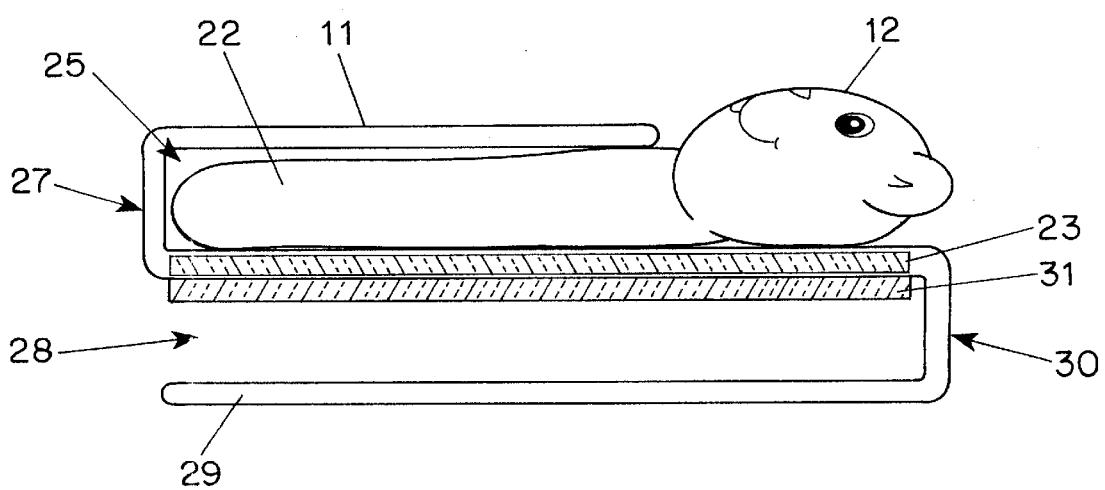
FIG. 2 is a cross-sectional view of the holder of FIG. 1.

Referring to FIGS. 1 and 2, the thermal compress holder is generally shown as 10. The holder comprises a flexible sheet or a plurality of flexible members formed into a flexible sheet. The flexible sheet is formed into a structure having two opposing pockets. Thus, a first pocket 25 is defined by a top portion 11 and a middle portion 23, which are sealed along the two peripheral edges 26 and 26' and the bottom edge 27. The second pocket 28 is defined by the middle portion 23 and a bottom portion 29, and is sealed along the peripheral edges 26 and 26' and at top edge 30. The edges may be sealed by folding, stitching, heat sealing, gluing or any other suitable means for joining the material(s) used in making the holder. The top, middle and bottom portions may be made from a continuous piece of the same material, from joined pieces of the same material or from joined pieces of different materials.

Pocket 25 is sized to receive a thermal compress 22. When the compress 22 is in the form of a novelty character, the pocket 25 is sized such that the head portion 12 of the novelty thermal compress 22 extends out of the pocket, thus resembling a sleeping bag with the head of the character extending out. Pocket 28 is sized to receive a human hand.

The compress holder 10 is made from a flexible fabric, which may be a woven or non-woven fabric, made from natural or synthetic materials. Suitable materials include terry cloth, knit fleece and other soft materials. The top portion 11 is preferably a thin fabric which protects the skin from burning or freezing while efficiently transferring heat or cold from the thermal compress to the injured area, and may include a metallized layer to enhance heat transfer. The middle portion is preferably an insulating material which reduces the transfer of heat or cold from the thermal compress into the first pocket. An extra layer of insulation 31 may be disposed along the middle portion 23 to provide further protection to a hand inserted into pocket 28 from being chilled or heated by a thermal.

Figure 3:
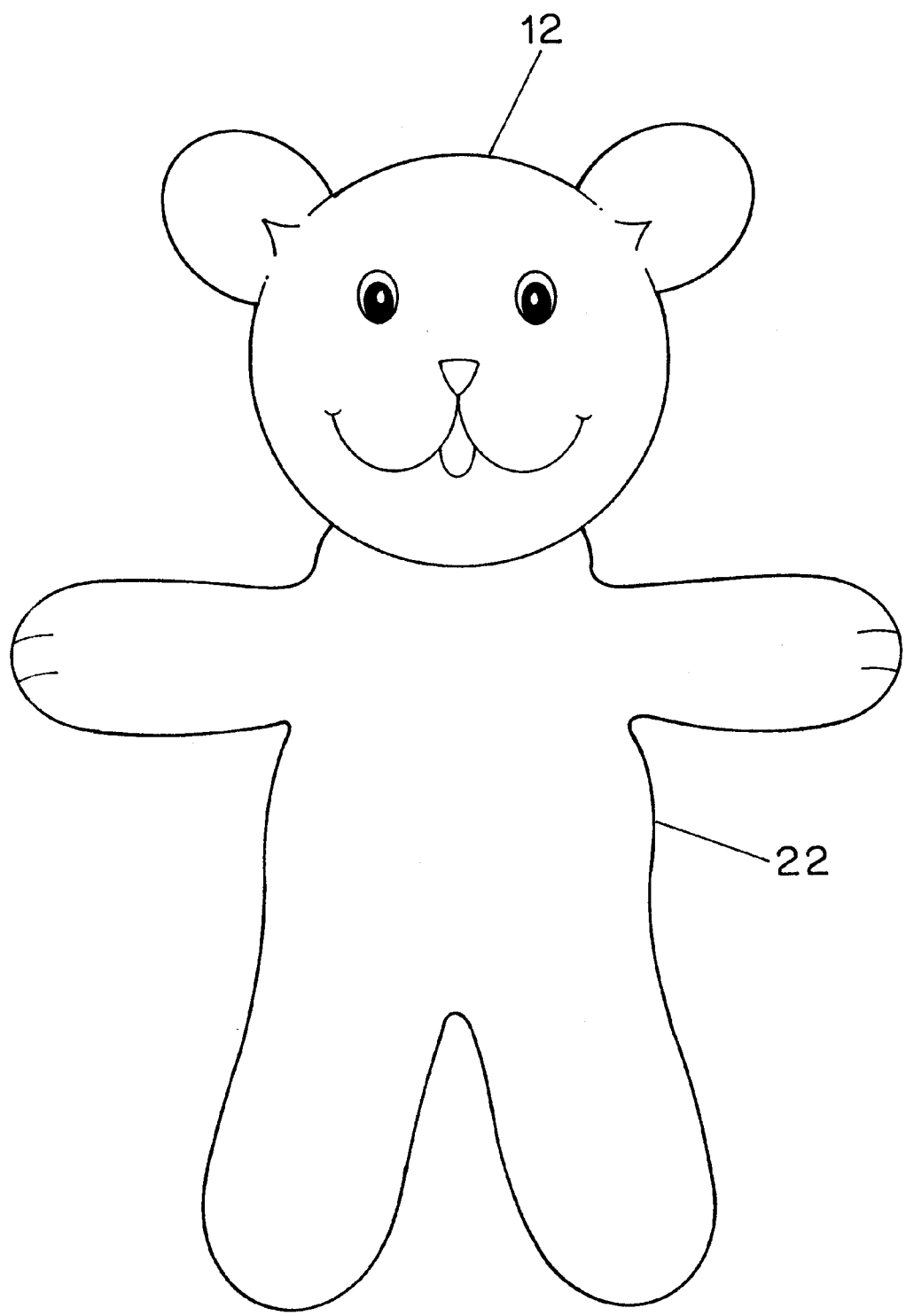
FIG. 3 is a front view of the novelty thermal compress of FIG. 1

While the novelty character shown in FIGS. 1–3 is a bear, it will be appreciated that the invention is not limited to any particular shape of thermal compress, or to the use of any particular type of novelty character. Thus, for example, other animals, including rabbits, birds, insects, cats, dogs, dinosaurs, cartoon characters and anthropomorphized inanimate objects might be use as novelty characters in the invention.

The holder of the invention may be packaged separately, or it may be packaged in a kit in combination with one or more thermal compresses. The compress and the holder packaged together are compatibly sized so that the compress fits snugly within one pocket of the holder.

Although the preferred embodiment of the apparatus of the invention has been described above in some detail, it should be appreciated that a variety of embodiments will be readily apparent to one skilled in the art. The description of the apparatus of this invention is not intended to be limiting to this invention, but is merely illustrative of the preferred embodiment.

I claim:

1. A thermal compress holder comprising a flexible sheet defining two pockets, each sealed on three sides and open on a fourth side, a first pocket for receiving a thermal compress and a second pocket for receiving a human hand, wherein the first pocket is open along a first edge of the holder and the second pocket is open along a second edge of the holder disposed opposite the first edge; wherein the first pocket is defined by a top portion and a middle portion of the fabric sheet, and the second pocket is defined by the middle portion and a bottom portion of the flexible sheet; the thermal compress holder further comprising an insulation layer disposed on the middle portion of the flexible sheet to provide a thermal insulation barrier between the first pocket and the second pocket.

2. The holder of claim 1, wherein the top portion is shorter than the middle portion, such that the first pocket is shorter in length than the holder.

3. The holder of claim 1, wherein the flexible sheet is formed from woven or non-woven fabric.

4. A thermal compress kit, comprising a thermal compress and a thermal compress holder, wherein the thermal compress holder comprises a flexible sheet defining two pockets, each sealed on three sides and open on a fourth side, a first pocket for receiving the thermal compress and a second pocket for receiving a human hand, wherein the first pocket is open along a first edge of the holder and the second pocket is open along a second edge of the holder disposed opposite the first edge; wherein the first pocket is defined by a top portion and a middle portion of the fabric sheet, and the second pocket is defined by the middle portion and a bottom portion of the flexible sheet; the thermal compress holder further comprising an insulation layer disposed on the middle portion of the flexible sheet to provide a thermal insulation barrier between the first pocket and the second pocket.

5. The kit of claim 4 wherein said flexible sheet is a woven or non-woven fabric.

6. The kit of claim 4, wherein the thermal compress is designed in the shape of a novelty character.

7. The kit of claim 6, wherein the novelty character has a defined head region, and wherein the first pocket is sized such that the head region of the thermal compress extends out of the pocket when the compress is fully inserted into the pocket.

8. The kit of claim 6, wherein the flexible sheet is formed from woven or non-woven fabric.

9. The kit of claim 4, wherein the top portion is shorter than the middle portion, such that the first pocket is shorter in length than the holder.

10. The kit of claim 4 wherein said thermal compress is an instant chemical compress.

11. The kit of claim 4 wherein said thermal compress is a microwavable compress.

12. A method for the treatment of bodily injuries with heat or cold comprising heating or cooling a thermal compress, inserting said compress into a holder, and placing the holder on the site of the injury; wherein said holder comprises a flexible sheet defining two pockets, each sealed on three sides and open on a fourth side, a first pocket for receiving a thermal compress and a second pocket for receiving a human hand, wherein the first pocket is open along a first edge of the holder and the second pocket is open along a second edge of the holder disposed opposite the first edge; wherein the first pocket is defined by a top portion and a middle portion of the fabric sheet, and the second pocket is defined by the middle portion and a bottom portion of the flexible sheet; the thermal compress holder further comprising an insulation layer disposed on the middle portion of the flexible sheet to provide a thermal insulation barrier between the first pocket and the second pocket.

13. The method of claim 12, wherein the thermal compress is designed in the shape of a novelty character.

14. The method of claim 13, wherein the novelty character has a defined head region, and wherein the first pocket is sized such that the head region of the thermal compress extends out of the pocket when the compress is fully inserted into the pocket.

15. The method of claim 14, wherein the top portion is shorter than the middle portion, such that the first pocket is shorter in length than the holder.

* * * * *